United States Patent [19]

Kure et al.

[11] Patent Number: 5,271,926

[45] Date of Patent: Dec. 21, 1993

[54] TWO-PACK HAIR TREATMENT COMPOSITION AND PROCESS FOR TREATING HAIR

[75] Inventors: Naohisa Kure, Tokyo; Noriko Saito, Funabashi; Yuji Hirano, Chiba, all of Japan

[73] Assignee: KAO Corporation, Tokyo, Japan

[21] Appl. No.: 853,996

[22] Filed: Mar. 19, 1992

[30] Foreign Application Priority Data

Apr. 4, 1991 [JP] Japan .................. 3-099624

[51] Int. Cl.$^5$ ............................................. A61K 7/075
[52] U.S. Cl. ...................................... 424/71; 424/70; 424/72
[58] Field of Search ...................... 424/72, 71, 70; 132/204, 209

[56] References Cited

U.S. PATENT DOCUMENTS

| 3,651,931 | 3/1972 | Hsiung | 424/72 |
|---|---|---|---|
| 3,823,232 | 7/1974 | Galerne | 132/204 |
| 3,912,808 | 10/1975 | Sokol | 424/72 |
| 4,139,610 | 2/1979 | Miyazaki et al. | 424/72 |
| 4,366,827 | 1/1983 | Madrange et al. | 132/204 |
| 4,638,822 | 1/1987 | Grollier et al. | 132/209 |

FOREIGN PATENT DOCUMENTS

| 0432051 | 6/1991 | European Pat. Off. . |
|---|---|---|
| 0461526 | 12/1991 | European Pat. Off. . |
| 0488242 | 6/1992 | European Pat. Off. . |
| 56-2812 | 7/1981 | Japan . |
| 56-100710 | 8/1981 | Japan . |
| 0083608 | 5/1983 | Japan . |
| 58-150506 | 9/1983 | Japan . |
| 64-75411 | 3/1989 | Japan . |
| 2063671 | 6/1981 | United Kingdom . |
| 2066310 | 7/1981 | United Kingdom . |
| 2114616 | 8/1983 | United Kingdom . |
| 2114616A | 8/1983 | United Kingdom . |

OTHER PUBLICATIONS

Patent Abstract of Japan, vol. 14, No. 100 (C-693) (4043) Feb. 23, 1990 & JP-A-13 08 215 (KAO).

*Primary Examiner*—Thurman K. Page
*Attorney, Agent, or Firm*—Birch, Stewart, Kolasch & Birch

[57] ABSTRACT

A two-pack hair treatment composition comprising a first lotion containing a reducing substance (a) and a cationic polymer (b) and a second lotion containing an anionic surfactant or amphoteric surfactant (c) and a lubricant (d), wherein the first lotion is applied to the hair first and then the second lotion is applied thereto.

The process of the present invention for treating the hair with the above-described two-pack hair treatment composition comprises treating the hair with the first lotion, leaving the hair to stand for a predetermined period of time and, if necessary, subjecting it to intermediate rinsing, applying the second lotion to the hair, leaving the hair stand again for a predetermined period of time, and finally rinsing the hair.

4 Claims, No Drawings

TWO-PACK HAIR TREATMENT COMPOSITION AND PROCESS FOR TREATING HAIR

BACKGROUND OF THE INVENTION

1. Field of the Invention

The present invention relates to a two-pack hair treatment composition having conditioning effects, in particular, the effects of imparting softness, moistness and smoothness to the hair and the effect of dressing the hair which tends to scatter, the conditioning effects lasting semipermanently. The present invention is also directed to a process for treating the hair with the two-pack hair treatment composition.

2. Description of the Prior Art

The most popular method for imparting softness, moistness and smoothness to the hair is the application of a conditioner, such as a rinse or treatment after shampooing at home. Treating the hair with such a conditioner causes the deposition of conditioning ingredients such as a cationic polymer, cationic surfactant, lubricant, silicone derivative, humectant, protein and its hydrolyzate, and animal and vegetable extracts, on the surface of the hair or in the surface layer thereof. In beauty salons and the like, efforts are being made to obtain better feeling than that obtained by using a household conditioner, by depositing a larger amount of the ingredients on the hair by an improved technique such as the use of a heater, e.g. a steamer, even when a conditioner having an effect substantially equivalent to that of a household conditioner is used. However, the conditioning effect thus obtained is only temporary, and it is removed after shampooing only once or twice. However, in today's society the frequency of shampooing is increasing and it is now habitually conducted about once a day, although this depends to a large extent on the generation. The conditioning effect is almost completely removed by the first shampooing after the treatment, and the hair cannot be sufficiently protected from physical damages caused by the friction of the hair or its entanglement in daily shampooing. Thus the damage to hair caused by shampooing is now becoming a serious problem.

Japanese Patent Laid-Open No. 75411/1989 discloses a hair treatment of the heating type, comprising the use of a composition containing a cationic polymer and a cysteine derivative, and heat treatment. With this treatment, the touch of the hair can be semipermanently improved in a relatively short time, the hair can be semipermanently waved, and the damage to the hair can be relieved. However, this treatment has an insufficient moistening effect under dry conditions and does not to impart sufficient softness and moistness to the hair.

Japanese Patent Laid-Open Nos. 100710/1981 and 150506/1983 discloses a permanent waving process wherein the first lotion comprising a reducing composition containing a cationic polymer was applied to the hair, and then the second lotion comprising an oxidizing composition containing an anionic surfactant was applied thereto. They also disclosed that the composition used in this process could impart a conditioning effect, such as a softening effect, to the hair. However, the process and composition disclosed therein were still insufficient in the persistence of the conditioning effect.

SUMMARY OF THE INVENTION

Therefore, an object of the present invention is to provide a two-pack hair treatment composition having conditioning effects, in particular, the effects of imparting softness, moistness and smoothness to the hair, and the effect of dressing the hair which tends to scatter, the conditioning effects last semipermanently. The present invention is also concerned with a process for treating the hair with the two-pack hair treatment composition.

After intensive investigations, the inventors have found that the above-described objects can be attained by treating the hair with a first lotion, comprising a reducing substance (a) and a cationic polymer (b), and then treating the hair with a second lotion, comprising an anionic or amphoteric surfactant (c) and a lubricant (d). The present invention has been completed on the basis of this finding.

Thus the present invention provides a two-pack hair treatment composition characterized by a first lotion comprising a reducing substance (a) and a cationic polymer (b), and a second lotion comprising an anionic or amphoteric surfactant (c) and a lubricant (d), the first lotion being applied to the hair first and then the second lotion being applied thereto.

The present invention provides also a process for treating the hair with the above-described two-pack hair treatment composition of the present invention, said process comprising treating the hair with the first lotion, leaving the hair to stand for a predetermined period of time, then applying the second lotion thereto, after, if necessary, an intermediate rinsing, leaving the hair again to stand for a predetermined period of time, and finally rinsing the hair.

The two-pack hair treatment composition of the present invention provides conditioning effects, in particular, the effects of imparting softness, moistness and smoothness to the hair, and the effect of dressing the hair, which tends to scatter, the conditioning effects lasting semipermanently.

DETAILED DESCRIPTION OF THE INVENTION

The reducing substance (a) in the first lotion constituting the two-pack hair treatment composition of the present invention includes those ordinarily contained in hair treatments, such as thioglycolic acid and salts thereof, preferably those with ammonium, an alkanol amine, such as monoethanolamine or triethanolamine, an alkali metal, such as sodium or potassium, or an alkaline earth metal such as calcium, cysteine and salts thereof; preferably hydrochlorides, cysteine derivatives, such as N-acetyl-L-cysteine; thiolactic acid and salts thereof, preferably those with ammonium, monoethanolamine, triethanolamine, or an alkali metal, such as sodium or potassium; sulfurous acid and salts thereof, preferably those with ammonium or an alkali metal, such as sodium or potassium; hydrogensulfites, preferably those with ammonium or an alkali metal, such as sodium or potassium. Among them, cysteine derivatives such as N-acetyl-L-cysteine, sulfurous acid and salts thereof, and hydrogensulfites are preferred.

The ingredients (a) can be used either singly or in combination. The amount thereof used is 0.05 to 1.5% by weight (hereinafter abbreviated to "%"), preferably 0.1 to 1.0%, based on the first lotion. If the amount of this ingredient (a) is insufficient, the conditioning effect cannot last for a long period of time and, on the other hand, when the amount is excessive, for example, when thioglycolic acid or a salt thereof is used in a high pH region, the hair will be damaged, due to a lowering of the elasticity and a flowing out of the protein from the hair, although the damage varies depending on the type of the reducing substance.

The cationic polymer (b) in the first lotion of the present invention includes water-soluble cationic polymers described in Japanese Patent Laid-Open No. 92812/1981 and homopolymers of an amino acid, such as dimer and higher polymers of lysine, which is basic amino acid. Examples of the cationic polymers include quaternary derivatives of cellulose ethers, water-soluble copolymers, quaternized polymers, vinyl-pyrrolidone copolymers and cationic polymer such as polylysine, described in Japanese Patent Laid-Open No. 75411/1989 (from line 20 in the left lower column of page 2 to line 12 in left upper column of page 5), quaternized polyvinylamine polymers and copolymers, described in Japanese Patent Laid Open No. 150506/1983 (lines 3 to 14 in the right lower column of page 3), quaternized poly-4-vinylpyridine polymers, described in Japanese Patent Laid-Open No. 150506/1983, and amino-modified silicone polymers, which will be described below.

The amino-modified silicone polymers are polymers of organosiloxanes having at least one aminoalkyl group in the molecule.

The organosiloxane forming the amino-modified silicone polymers usually contains a methyl group as a functional group other than an aminoalkyl group. It can further contain an alkyl group, such as an ethyl or propyl group; an alkenyl group, such as a vinyl or allyl group; an aryl group, such as a phenyl or naphthyl group; a cycloalkyl group, such as a cyclohexyl group; and hydroxy, hydroxyalkyl, hydroxyalkylene and polyoxyalkylene groups.

Typical examples of the aminoalkyl groups contained in the amino-modified silicone polymer are represented by the following formula 1 or 2:

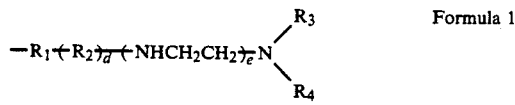 Formula 1 wherein $R_1$ represents a divalent hydrocarbon group, $R_2$ represents

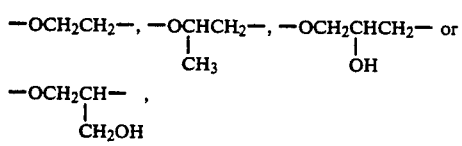

$R_3$ and $R_2$ each represent a hydrogen atom or a monovalent hydrocarbon group, and d and e each represent an integer of 0 to 6.

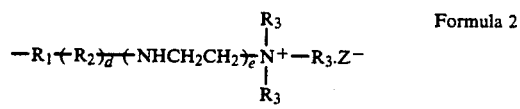 Formula 2 wherein $R_1$ represents a divalent hydrocarbon group, $R_2$ represents

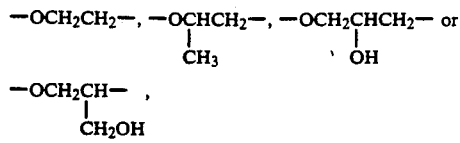

$R_3$ represents a hydrogen atom or a monovalent hydrocarbon group, d and e each represent an integer of 0 to 6, and $Z^-$ represents a halogide ion or organic anion.

Examples of the divalent hydrocarbon group $R_1$ in the above formulae 1 and 2 include alkylene groups such as methylene, ethylene, propylene, butylene and $-CH_2CH(CH_3)CH_2-$ and alkylenearylene groups such as $-(CH_2)_2C_6H_4-$. Among them, alkylene groups, particularly a propylene group, is preferred. The monovalent hydrocarbon groups $R_3$ and $R_4$ include methyl, ethyl, propyl, hexyl and phenyl groups. Both $R_3$ and $R_4$ may be a hydrogen atom or the monovalent hydrocarbon group or, alternatively, $R_3$ may be a hydrogen atom and $R_4$ may be the monovalent hydrocarbon group. Preferred values of d and e are 0 and 1, respectively.

Typical examples of the hydroxyalkyl groups are represented by the following general formula:

$$-R_1OH-$$

wherein $R_1$ is as defined above.

Typical examples of the hydroxyalkylene and polyoxyalkylene groups are represented by the following formula 3:

 Formula 3 wherein $R_1$ is as defined above, f represents 0 or 1, g represents an integer of 1 to 100, and h represents an integer of 1 to 5.

Among the hydroxyalkyl groups of the above formula 3, preferred are those wherein f is 1, g is an integer of 3 to 70 and h is 2 or 3. The hydroxyalkyl groups wherein h is 2 or 3 may be bonded together in block or at random. The same will apply when h represents another integer.

Typical amino-modified silicone polymers are those of the following formula 4 or 5:

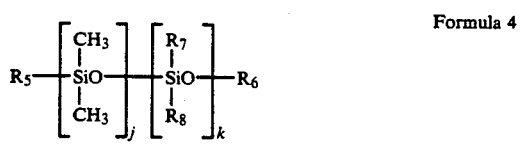 Formula 4 wherein $R_5$ represents a methyl or hydroxyl group, $R_6$ represents a methyl group or a hydrogen atom, $R_7$ represents an aminoalkyl group of the above formula 1 or 2, $R_6$ represents a hydroxy, hydroxyalkyl, hydroxyalkylene or polyoxyalkylene group, and j and k each represent an integer which varies depending on the molecular weight.

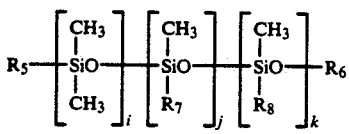

Formula 5 wherein $R_5$ represents a methyl or hydroxyl group, $R_6$ represents a methyl group or a hydrogen atom, $R_7$ represents an aminoalkyl group of the above formula 1 or 2, $R_8$ represents a hydroxy, hydroxyalkyl, hydroxyalkylene or polyoxyalkylene group, and i,j and k each represent an integer which varies depending on the molecular weight.

Among them, particularly preferred amino-modified silicone polymers are those of the following formula 6:

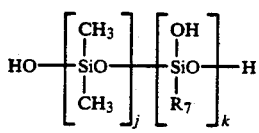

Formula 6 wherein $R_7$ represents an aminoalkyl group of the above formula 1 or 2, and j and k each represent an integer which varies depending on the molecular weight.

Typical examples of the amino-modified silicone polymers of the present invention are those of the following formula 7 having an average molecular weight of about 3,000 to 100,000, which are called "Amodimethicone" [see CTFA dictionary (Cosmetic Ingredient Dictionary), the third edition (U.S.A.)]:

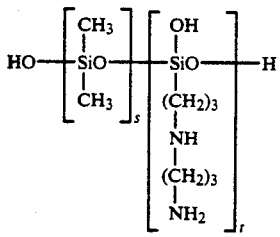

Formula 7 wherein s and t each represent an integer which varies depending on the molecular weight ranging from 300,000 to 100,000.

The ingredient (b) can be used either singly or in combination. The amount of the ingredient (b) is 0.1 to 25.0%, particularly preferably 1.0 to 15.0%, based on the first lotion. When the amount of the ingredient (b) is insufficient, it is difficult to form a complex capable of imparting softness, moistness and water retention to the hair and, on the contrary, when it is excessive, the softness and wiriness of the hair becomes insufficient due to the adsorption of an excessive cationic polymer.

The pH of the first lotion comprising the ingredients (a) and (b) is preferably 3.0 to 8.5, particularly 4.0 to 8.0. When it is below 3.0, any preferred reducing substance having a reducing capacity necessary for or effective in the present invention and capable of being used for the production of a stable preparation cannot be obtained in this pH range. When the pH of the first lotion is above 8.5, the hair tends to be damaged by an increased reactivity of the reducing substance, and the hair is swollen by the alkali to further increase the damage.

The anionic and amphoteric surfactants used as the component (c) in the second lotion constituting the two-pack hair treatment composition of the present invention include those described below.

Anionic Surfactants (1) Linear or branched alkylbenzenesulfonates having an alkyl group having 10 to 16 carbon atoms on average.

(2) Alkyl or alkenyl ether sulfates having a linear or branched alkyl or alkenyl group having 10 to 20 carbon atoms on average, and 0.5 to 8 mol on average of ethylene oxide, propylene oxide, butylene oxide, or both ethylene oxide and propylene oxide in a molar ratio of 0.1/9.9, to 9.9/0.1 or both ethylene oxide and butylene oxide in a molar ratio of 0.1/9.9, to 9.9/0.1 added thereto in the molecule.

(3) Alkyl or alkenylsulfates having an alkyl or alkenyl group having 10 to 20 carbon atoms on average.

(4) Olefinsulfonates having 10 to 20 carbon atoms on average in the molecule.

(5) Alkanesulfonates having 10 to 20 carbon atoms on average in the molecule.

(6) Saturated or unsaturated fatty acid salts having 10 to 24 carbon atoms on average in the molecule.

(7) Alkyl or alkenyl ether carboxylates having an alkyl or alkenyl group having 10 to 20 carbon atoms on average and 0.5 to 8 mol on average of ethylene oxide, propylene oxide, butylene oxide, or both ethylene oxide and propylene oxide in a molar ratio of 0.1/9.9 to 9.9/0.1, or both ethylene oxide and butylene oxide in a molar ratio of 0.1/9.9, to 9.9/0.1 added thereto in the molecule.

(8) α-Sulfo fatty acid salts or esters having an alkyl or alkenyl group having 10 to 20 carbon atoms, on average.

(9) N-Acylamino acid surfactants having an acyl group having 8 to 24 carbon atoms and a free carboxylic acid or sulfonic acid residue.

(10) Phosphoric mono- or diester surfactants having an alkyl or alkenyl group having 8 to 24 carbon atoms, or an ethoxylate thereof.

(11) Sulfosuccinic esters of a higher alcohol having 8 to 22 carbon atoms, or its ethoxylate or sulfosuccinic esters derived from a higher fatty acid amide.

(12) Sulfonic acid salts of a monoethanolamide, diethanolamide or ethoxylate of a higher fatty acid having 8 to 20 carbon atoms.

(13) Sulfonates of a monoglyceride having 8 to 20 carbon atoms.

(14) Salts of a condensate of a higher fatty acid having 8 to 20 carbon atoms with isethionic acid.

Amphoteric Surfactants

(15) Imidazoline amphoteric surfactants of a secondary or tertiary amide type and α-position addition type having an alkyl, alkenyl or acyl group having 8 to 24 carbon atoms.

(16) Carbobetaine, amidebetaine, sulfobetaine, hydroxysulfobetaine, or amidesulfobetaine amphoteric surfactants having an alkyl, alkenyl or acyl group having 6 to 24 carbon atoms.

Among the above-described components (c), the following compounds ① to ⑥ are preferred:

① N-acyl-L-glutamic acids and salts thereof of the following formula 8:

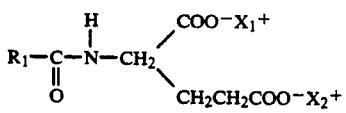

Formula 8 wherein $R_1$ represents a straight chain or branched alkyl or an alkenyl group having 12 to 18 carbon atoms, and $X_1$ and $X_2$, which may be the same or different from each other, each represent hydrogen, potassium, sodium or triethanolamine salt, ② aminoalkyltauric acids and salts thereof of the following formula 9:

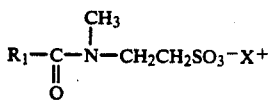

Formula 9 wherein $R_1$ represents a straight-chain or branched alkyl or an alkenyl group having 12 to 18 carbon atoms, $R_2$ represents a straight-chain alkyl group having 1 to 3 carbon atoms and X represents hydrogen, potassium, sodium or triethanolamine salt, ③ amide ether sulfates and salts thereof of the following formula 10:

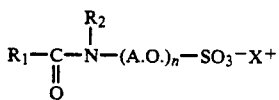

Formula 10 wherein $R_1$ represents a straight-chain or branched alkyl or an alkenyl group having 12 to 18 carbon atoms, $R_2$ represents a straight-chain alkyl group having 1 to 3 carbon atoms, to which 1 to 5 molecules on average (=n) of ethylene oxide, propylene oxide or butylene oxide (A.O.) is added, and X represents hydrogen, potassium, sodium or triethanolamine salt, ④ monoalkyl or dialkylphosphoric acids and salts thereof of the following formula 11:

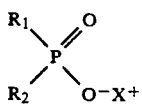

Formula 11 wherein $R_1$ represents a straight-chain or branched alkyl or an alkenyl group having 12 to 18 carbon atoms, $R_2$ represents hydrogen or a straight-chain or branched alkyl or an alkenyl group having 12 to 18 carbon atoms, and X represents hydrogen, potassium, sodium or triethanolamine salt (when $R_2$ represents hydrogen, it is a monoalkylphosphoric acid or a salt thereof), ⑤ secondary amide type or tertiary amide type imidazoline amphoteric surfactants and salts thereof of the following formulae 12, 13 and 14:

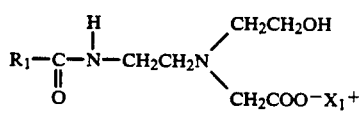

Formula 12 wherein $R_1$ represents a straight-chain or branched alkyl or an alkenyl group having 7 to 18 carbon atoms, and X represents hydrogen, potassium, sodium or triethanolamine salt,

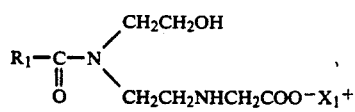

Formula 13 wherein $R_1$ represents a straight-chain or branched alkyl or alkenyl group having 7 to 18 carbon atoms, and $X_1$ represents hydrogen, potassium, sodium or triethanolamine salt,

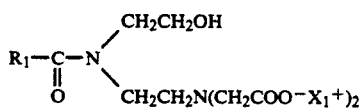

Formula 14 wherein $R_1$ represents a straight-chain or branched alkyl or alkenyl group having 7 to 18 carbon atoms and $X_1$ represents hydrogen, potassium, sodium or triethanolamine salt, ⑥ carbobetaine, sulfobetaine and hydroxysulfobetaine amphoteric surfactants of the following formulae 15 and 16:

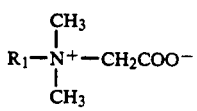

Formula 15 wherein $R_1$ represents an alkyl, alkenyl or acyl group having 6 to 24 carbon atoms,

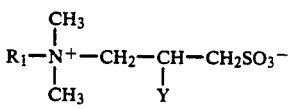

Formula 16 wherein $R_1$ represents an alkyl, alkenyl or acyl group having 6 to 24 carbon atoms and Y represents hydrogen or a hydroxyl group.

The ingredients (c) can be used either singly or in combination. The amount thereof is 0.1 to 15.0%, particularly preferably 1.0 to 10.0%, based on the second lotion. When the amount of this ingredient is insufficient, any complex sufficient for imparting the conditioning effect to the hair cannot be easily formed and, on the contrary, when it is excessive, the complex is dissolved again and any sufficient conditioning effect on the hair cannot be obtained. In addition, when the anionic surfactant as the ingredient (c) is used in a large amount, the workability, such as defoamability, in the final rinsing step is impaired.

The lubricant used as the ingredient (d) of the second lotion in the present invention may be any of liquid and solid lubricants ordinarily used for cosmetics. Particularly preferred is an amphipathic lipid or nonionic surfactant capable of forming a stable emulsion together with the anionic or amphoteric surfactant (c).

The amphipathic lipids are substances having both hydrophobic and hydrophilic moieties in the molecule, such as higher fatty acids, higher alcohols, cholesterols and fatty acid esters thereof, mono- and dialkyl glyceryl ethers, glycerides, phospholipids, ceramides and derivatives thereof. The term "higher alcohols" herein indicates compounds of the general formula: R-OH wherein R preferably represents a straight-chain alkyl or alkenyl group having 12 to 24 carbon atoms or a branched alkyl or alkenyl group having 20 to 42 carbon atoms.

The nonionic surfactants are preferably the following compounds ① to ⑤;

① polyoxyalkylene alkyl ethers or polyoxyalkylene alkenyl ethers having a straight-chain or branched alkyl or alkenyl group having 8 to 24 carbon atoms on average which are in the form of an adduct with ethylene oxide, propylene oxide or butylene oxide, ② alkyl saccharide surfactants having a straight chain or branched alkyl, alkenyl or alkylphenyl group having 8 to 18 carbon atoms, ③ alkylamine oxides or alkylamide oxides having a straight chain or branched alkyl or alkenyl group having 8 to 20 carbon atoms, ④ polyoxyethylene sorbitan fatty acid esters having an acyl group having 8 to 20 carbon atoms, and ⑤ polyoxyethylene sorbitol fatty acid esters having an acyl group having 8 to 18 carbon atoms.

The ingredient (d) can be used either singly or in combination in an amount of preferably 2.5 to 25.0%, particularly 2.5 to 10.0%, based on the second lotion. When the amount of the ingredient (d) is insufficient, it is difficult to form a stable emulsion together with the anionic or amphoteric surfactant (c) and, on the contrary, when the amount is excessive, the second lotion applied to the hair cannot be thoroughly mixed with the first lotion and, therefore, any complex cannot be effectively formed.

The first and second lotions in the two-pack hair treatment composition of the present invention may suitably contain ordinary additives for cosmetics, such as a medicine, chelating agent, pearling agent, flavor, colorant, ultraviolet absorber, a germicide, such as triclosan or triclocarban, an antiinflammatory agent, such as potassium glycyrrhizate or tocopherol acetate, a dandruff inhibitor, such as zinc pyrithione or Piroctone Auramine, and anitseptic, such as methylparaben or butylparaben, as well as a solvent for solubilizing the hair treatment composition, so far as the object of the present invention can be attained.

The two-pack hair treatment composition of the present invention is applied to the hair as follows: the hair is first treated with the first lotion and preferably left to stand at 40 to 80° C. for a predetermined period of time, i.e., about 5 to 30 min, preferably about 10 min. The second lotion is applied to the hair directly, or after intermediate rinsing. Preferably, the hair is again left to stand for a predetermined period of time, i.e., about 5 to 20 min, preferably about 5 min, and finally rinsed.

In the application of the two-pack hair treatment composition of the present invention to the hair, it is preferred to heat the hair at 40° to 80° C. for 5 to 30 min during the treatment with the first lotion in order to further improve the effect. When the temperature is below 40° C., no sufficient effect can be obtained and, on the contrary, when it exceeds 80° C., the hair is damaged. When the heating time is shorter than 5 min, no sufficient effect can be obtained and, on the contrary, even when it exceeds 30 min, the effect is no more improved.

When the hair is treated with the two-pack hair treatment composition of the present invention, the cationic polymer deposited on the hair by the treatment with the first lotion forms a complex with the anionic surfactant or amphoteric surfactant in the second lotion so that the cationic polymer is firmly adsorbed on the hair and protected by the emulsion of the second lotion electrically adsorbed on the polymer. The durability in shampooing is remarkably improved, a large amount of water is kept in a hydrophilic area between the cationic polymer and the emulsion of the second lotion by the formation of the complex, which area acts as a buffering layer against the evaporation of water from the hair and, therefore, the hair has a sufficient softness, moistness and smoothness, even in a dry atmosphere, and drying and untidy spread of the hair can be prevented. Such conditioning effects last semipermanently.

The following Examples and Comparative Examples will further illustrate the present invention, but by no means should be considered to limit the scope of the invention.

EXAMPLE 1 AND COMPARATIVE EXAMPLE 1

Two-pack hair treatment compositions 1 and 2 of the present invention and comparative compositions 1 to 5 specified in the following Table 1 are prepared. The concentration of each ingredient given in this Table refers to that of the active ingredient.

The effect of each of the hair treatment compositions applied to the hair is evaluated by a method which will be described below. The results are given in Table 2.

Evaluation Method (1) The first lotion of the hair treatment composition is applied to 0.7 g of a bundle (length: 15 cm) of shampooed ordinary Japanese hair at a bath ratio (weight ratio of the hair to the treatment) of 1:1. Then the hair is heated at 50° C. for 10 min and the second lotion was applied thereto at a bath ratio of 1:1. After being left to stand at room temperature for 5 min, the hair is rinsed with running water and dried. The hair thus treated will be referred to as "hair directly after the treatment". The hair is then shampooed and dried 10 times under ordinary conditions. The hair thus treated is referred to as "hair shampooed 10 times". The quantity of quaternary nitrogen, that is, the quantity of adsorbed cation on the surface of the hair is determined as follows.

Method of Determining Quaternary Nitrogen

The state of nitrogen on the surface of the hair, namely, the percentage of the quaternary nitrogen based on the total nitrogen on the surface of the hair, is analyzed directly after the treatment and after shampooing 10 times with an electron spectroscopy surface analyzer (ESCA).

(2) The hair directly after the treatment and the hair shampooed 10 times obtained in the above step (1) are evaluated as will be described below. The term "control hair" which will be described below is an untreated hair as compared with the hair directly after the treatment, or the hair obtained after shampooing the untreated hair 10 times as compared with the hair shampooed 10 times.

(1) Softness of hair:
⊙: far softer than the control hair,
○: significantly softer than the control hair,
Δ: slightly softer than the control hair, and
X: equivalent to the control hair.

(2) Moistness of hair:
⊙: far moister than the control hair,
○: significantly moister than the control hair,
Δ: slightly moister than the control hair, and
X: equivalent to the control hair.

(3) Smoothness of hair:
⊙: far smoother than the control hair,
○: significantly smoother than the control hair, Δ: slightly smoother than the control hair, and
X: equivalent to the control hair.

TABLE 1

| Composition (wt. %) | Present invention 1 | Present invention 2 | Comparative 1 | Comparative 2 | Comparative 3 | Comparative 4 | Comparative 5 |
|---|---|---|---|---|---|---|---|
| The first lotion | | | | | | | |
| N-acetyl-L-cysteine | 0.5 | — | 0.5 | — | — | 0.5 | 0.5 |
| sodium hydrogensulfite | — | 0.5 | — | 0.5 | — | — | — |
| polydimethylethylenepiperdium chloride*1 | 10.0 | 10.0 | 10.0 | 10.0 | 10.0 | — | 10.0 |
| aqueous ammonia (28%) (pH modifier) | suitable amount | suitable amount | suitable amount | suitable amount | suitable amount | suitable amount | suitable amount |
| water | balance | balance | balance | balance | balance | balance | balance |
| pH | 7.0 | 4.0 | 7.0 | 4.0 | 7.0 | 7.0 | 7.0 |
| The second lotion | | | | | | | |
| propylene glycol | 5.0 | 5.0 | 5.0 | 5.0 | 5.0 | 5.0 | 3.0 |
| cetanol | 6.0 | 6.0 | — | — | 6.0 | 6.0 | 6.0 |
| sodium N-lauroyl-L-glutamate*2 | 3.5 | 3.5 | 3.0 | 3.5 | 3.5 | 3.5 | — |
| cetyltrimethylammonium chloride | — | — | — | — | — | — | 3.5 |
| water | balance | balance | balance | balance | balance | balance | balance |

*1 Merquat 100 [dimethyldiallylammonium chloride homopolymer (40 wt. % act.) (a product of Merck)]
*2 Amisoft LS-11 (monosodium lauroyl glutamate; a product of Ajinomoto Co., Inc.)

TABLE 2

| Results of evaluation | | Present invention 1 | Present invention 2 | Comparative 1 | Comparative 2 | Comparative 3 | Comparative 4 | Comparative 5 |
|---|---|---|---|---|---|---|---|---|
| immediately after the treatment | amount of quat. nitrogen | 30 | 35 | 27 | 33 | 22 | 0 | 30 |
| | softness | ⊚ | ⊚ | ○ | ○ | ○ | Δ | ○ |
| | moistness | ⊚ | ⊚ | ○ | ○ | ○ | Δ | ○ |
| | smoothness | ○ | ○ | ○ | ○ | ○ | Δ | ○ |
| after shampooing 10 times | amount of quat. nitrogen | 15 | 17 | 7 | 10 | 3 | 0 | 7 |
| | softness | ○ | ○ | Δ | Δ | x | x | x |
| | moistness | ⊚ | ⊚ | Δ | Δ | x | x | x |
| | smoothness | ⊚ | ⊚ | ○ | ○ | Δ | x | x |

EXAMPLE 2

The first lotion (1-1) specified below is applied to the hair. The hair is heated at 50° C. for 10 min. The second lotion (2-1) specified below is then applied thereto. After leaving the hair to stand at room temperature for 5 min, it is rinsed with running water. The hair is very soft, moist and smooth. This effect is substantially unchanged, even after shampooing 10 times.

EXAMPLE 3

The first lotion (1-2) specified below is applied to the hair. The hair is heated at 50° C. for 10 min. The second lotion (2-1) specified below is then applied thereto. After leaving the hair to stand at room temperature for 5 min, it is rinsed with running water. The hair is very soft, moist and smooth. This effect is substantially unchanged, even after shampooing 10 times.

EXAMPLE 4

The first lotion (1-3) specified below is applied to the hair. The hair is heated at 50° C. for 10 min and lightly rinsed with running water. The second lotion (2-1) specified below is then applied thereto. After leaving the hair to stand at room temperature for 5 min, it is rinsed with running water. The hair is very soft, moist and smooth. This effect is substantially unchanged, even after shampooing 10 times.

EXAMPLE 5

The first lotion (1-4) specified below is applied to the hair. The hair is heated at 50° C. for 10 min and lightly rinsed with running water. The second lotion (2-1) specified below is then applied thereto. After leaving the hair to stand at room temperature for 5 min, it is rinsed with running water. The hair is very soft, moist and smooth. This effect is substantially unchanged, even after shampooing 10 times.

EXAMPLE 6

The first lotion (1-1) specified below is applied to the hair. The hair is heated at 50° C. for 10 min. The second lotion (2-2) specified below is then applied thereto. After leaving the hair to stand at room temperature for 5 min, it is rinsed with running water. The hair is very soft, moist and smooth. This effect is substantially unchanged, even after shampooing 10 times.

EXAMPLE 7

The first lotion (1-2) specified below is applied to the hair. The hair is heated at 50° C. for 10 min. The second lotion (2-2) specified below is then applied thereto. After leaving the hair to stand at room temperature for 5 min, it is rinsed with running water. The hair is quite soft, moist and smooth. This effect is substantially unchanged, even after shampooing 10 times.

EXAMPLE 8

The first lotion (1-3) specified below is applied to the hair. The hair is heated at 40° C. for 20 min. The second lotion (2-2) specified below is then applied thereto. The hair is left to stand at room temperature for 5 min and rinsed with running water. The hair is very soft, moist and smooth. This effect is substantially unchanged, even after shampooing 10 times.

EXAMPLE 9

The first lotion (1-4) specified below is applied to the hair. The hair is heated at 70° C. for 5 min. The second lotion (2-2) specified below is then applied thereto. The hair is left to stand at room temperature for 5 min and rinsed with running water. The hair is very soft, moist and smooth. This effect is substantially unchanged, even after shampooing 10 times.

| (Examples of formulation of the first lotion) | |
|---|---|
| sodium N-lauroyl-L-glutamate | 4.0 |
| α-monoisostearyl glyceryl ether | 1.5 |
| sodium dl-pyrrolidonecarboxylate (50%) | 0.1 |
| hydroxyethylcellulose (Daicel SE 850)*2 | 0.1 |
| flavor | a suitable amount |

| | |
|---|---|
| colorant | a minute amount |
| water | the balance |
| in total | 100.0 wt % |

The second lotion (2-2)

| | |
|---|---|
| propylene glycol | 5.0 |
| cetanol | 6.0 |
| lauryldimethylaminoacetic acid betaine | 3.5 |
| α-monoisostearyl glyceryl ether | 1.5 |
| sodium dl-pyrrolidonecarboxylate (50%) | 0.1 |
| hydroxyethylcellulose (Daicel SE 850) | 0.1 |
| flavor | a suitable amount |
| colorant | a minute amount |
| water | the balance |
| in total | 100.0 wt % |

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A two-pack hair treatment composition comprising a first lotion having a pH of 3.0 to 8.5, containing:
   (a) 0.5 to 1.5% by weight of a reducing substance selected from the group consisting of thioglycolic acid and salts thereof, cysteine and salts thereof, cysteine derivative, thiolactic acid and salts thereof, sulfurous acid and salts thereof, and hydrogensulfites; and
   (b) 0.1 to 25.0% by weight of a cationic polymer selected from the group consisting of lysine dimer, lysine polymers, quaternary derivatives of cellulose ethers, vinyl-pyrrolidone copolymers, quaternized polyvinylamine polymers and copolymers, quaternized poly-4-vinylpyridine polymers, and amino-modified silicone polymers according to Formula (4) or Formula (5):

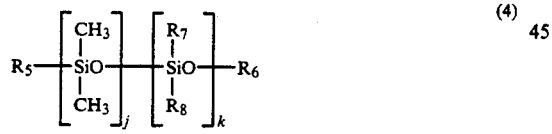

(4)

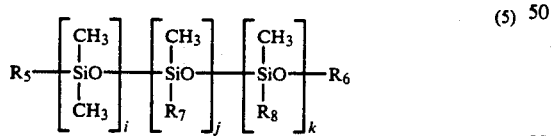

(5)

wherein $R_5$ is methyl or hydroxyl, $R_6$ is methyl or hydrogen, $R_8$ is hydroxy, hydroxyalkyl, hydroxyalkylene, or polyoxyalkylene, i, j and k each represent an integer which varies depending on molecular weight, and $R_7$ is an aminoalkyl group of Formula (1) or Formula (2):

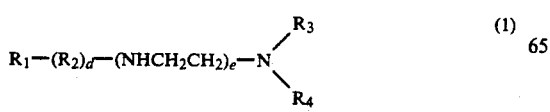

(1)

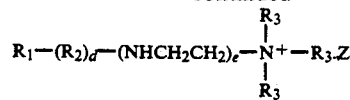

(2)

wherein $R_1$ is divalent hydrocarbyl, $R_2$ is $$-OCH_2CH_2-,\ -OCHCH_2-,\ -OCH_2CHCH_2-,\ \text{or}$$
$$\phantom{-OCH_2CH_2-,\ -O}CH_3\phantom{CH_2-,\ -OCH_2CH}OH$$

$$-OCH_2CH-,$$
$$\phantom{-OCH_2}CH_2OH$$

$R^3$ and $R^4$ each represent hydrogen or monovalent hydrocarbyl, d and e each represent an integer of 0 to 6, and Z is a halogide ion or organic anion; and a second lotion containing (c) 0.1 to 15.0% by weight of an anionic surfactant or amphoteric surfactant wherein said anionic or amphoteric surfactant is selected from the group consisting of linear or branched alkylbenzene sulfonates, alkyl or alkenyl ether sulfates, alkyl or alkenyl-sulfates, olefinsulfonates, alkanesulfonates, saturated or unsaturated fatty acid salts, alkyl or alkenyl ether carboxylates, α-sulfo fatty acid salts or esters, N-acylamino acids, phosphoric mono- or diesters, sulfosuccinic esters, sulfonic acid salts of a monoethanol-amide, diethanolamide, or ethoxylate of higher fatty acids, sulfonates of monoglycerides, salts of condensates of higher fatty acids with isethionic acid, secondary or tertiary amide imidazolines, carbobetaines, amide betaines, sulfobetaines, hydroxysulfobetaines, and amide sulfobetaines; and (d) 2.5 to 25.0% by weight of a lubricant selected from the group consisting of amphipathic liquids and nonionic surfactants.

2. A two-pack hair treatment composition comprising a first lotion containing:
   (a) 0.05 to 1.5% by weight of a reducing substance selected from the group consisting of thioglycolic acid and salts thereof, cysteine and salts thereof, cysteine derivative, thiolactic acid and salts thereof, sulfurous acid and salts thereof, and hydrogensulfites; and
   (b) 0.1 to 25.0% by weight of a cationic polymer selected from the group consisting of lysine dimer, lysine polymers, quaternary derivatives of cellulose ethers, vinylpyrrolidone copolymers, quaternized polyvinylamine polymers and copolymers, quaternized poly-4-vinylpyridine polymers, and amino-modified silicone polymers according to Formula (4) or Formula (5):

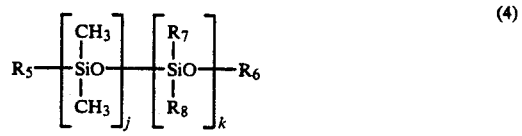

(4)

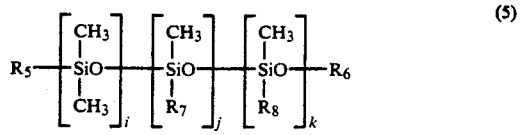

(5)

wherein $R_5$ is methyl or hydroxyl, $R_6$ is methyl or hydrogen, $R_8$ is hydroxy, hydroxyalkyl, hydroxyalkylene, or polyoxyalkylene, i, j and k each represent an integer which varies depending on molecular weight, and $R_7$ is an aminoalkyl group of Formula (1) or Formula (2):

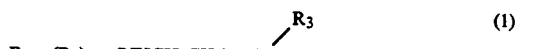

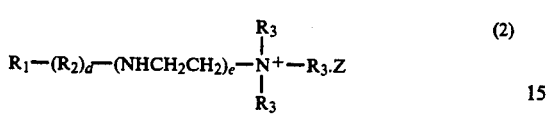

wherein $R_1$ is divalent hydrocarbyl, $R_2$ is

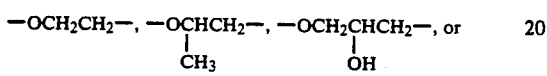

$R^3$ and $R^4$ each represent hydrogen or monovalent hydrocarbyl, d and e each represent an integer of 0 to 6, and Z is a halogide ion or organic anion; and a second lotion containing (c) 0.1 to 15.0% by weight of an anionic surfactant or amphoteric surfactant selected from the group consisting of:

1) N-acyl-L-glutamic acids and salts thereof of Formula (8):

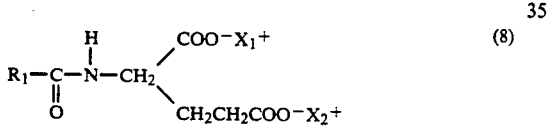

wherein $R_1$ is straight chain or branched alkyl or alkenyl having 12 to 18 carbon atoms, and $X_1$ and $X_2$, which may be the same or different from each other, are each hydrogen, potassium, sodium or triethanolamine salt;

2) aminoalkyltauric acids and salts thereof of Formula (9):

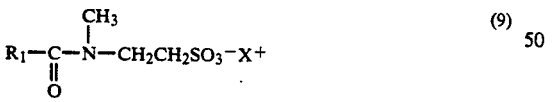

wherein $R_1$ is straight-chain or branched alkyl or alkenyl having 12 to 18 carbon atoms, $R_2$ is straight-chain alkyl having 1 to 3 carbon atoms and X is hydrogen, potassium, sodium or triethanolamine salt;

3) amide ether sulfates and salts thereof of Formula (10):

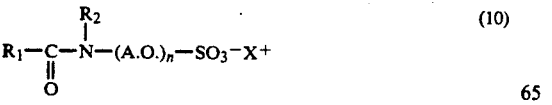

wherein $R_1$ is straight-chain or branched alkyl or alkenyl having 12 to 18 carbon atoms, $R_2$ is straight-chain alkyl having 1 to 3 carbon atoms, A.O. is ethylene oxide, propylene oxide, or butylene oxide, n is, on average, 1 to 5, and X is hydrogen, potassium, sodium or triethanolamine salt;

4) monoalkyl or dialkylphosphoric acids and salts thereof of Formula (11):

wherein $R_1$ is straight-chain or branched alkyl or alkenyl having 12 to 18 carbon atoms, $R_2$ is hydrogen or straight-chain or branched alkyl or alkenyl having 12 to 18 carbon atoms, and X is hydrogen, potassium, sodium or triethanolamine salt;

5) secondary amide type or tertiary amide type imidazoline amphoteric surfactants and salts thereof of Formula (12), (13) and (14):

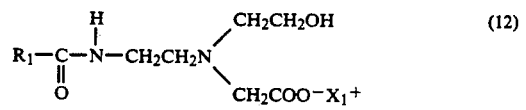

wherein $R_1$ is straight-chain or branched alkyl or alkenyl having 7 to 18 carbon atoms, and $X_1$ is hydrogen, potassium, sodium or triethanolamine salt;

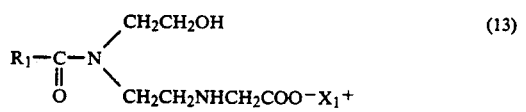

wherein $R_1$ is straight-chain or branched alkyl or alkenyl having 7 to 18 carbon atoms, and $X_1$ is hydrogen, potassium, sodium or triethanolamine salt;

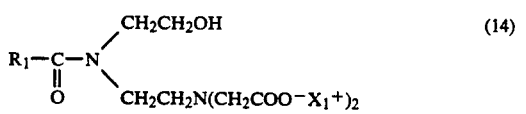

wherein $R_1$ is straight-chain or branched alkyl or alkenyl having 7 to 18 carbon atoms, and $X_1$ is hydrogen, potassium, sodium or triethanolamine salt;

6) carbobetaine, sulfobetaine and hydroxy-sulfobetaine amphoteric surfactants of Formulae (15) and (16):

wherein $R_1$ is alkyl, alkenyl or acyl having 6 to 24 carbon atoms; and

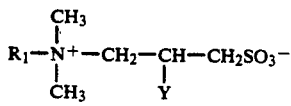

(16)

wherein R₁ is alkyl, alkenyl or acyl having 6 to 24 carbon atoms and Y is hydrogen or hydroxyl; and (d) 2.5 to 25.0% by weight of a lubricant selected from the group consisting of amphipathic liquids and nonionic surfactants.

3. The two-pack hair treatment composition according to claim 1, wherein said amphipatic liquids are selected from the group consisting of higher fatty acids, higher alcohols, cholesterols and fatty acid esters thereof, mono- and dialkyl glyceryl ethers, glycerides, phospholipids, ceramides and derivatives thereof.

4. The two-pack hair treatment composition according to claim 1, wherein said nonionic surfactants are selected from the group consisting of polyoxyalkylene alkyl ethers, polyoxyalkylene, alkenyl ethers, alkylsaccharides, alkylamine oxides, alkylamide oxides, polyoxyethylene sorbitan fatty acid esters having an acyl group of 8 to 20 carbon atoms, and polyoxyethylene sorbitol fatty acid esters having an acyl group of 8 to 18 carbon atoms.

* * * * *